United States Patent [19]

Moon et al.

[11] 3,932,662

[45] Jan. 13, 1976

[54] METHOD OF TREATING ANIMALS AND FORMULATIONS THEREFOR

[75] Inventors: Malcolm W. Moon; Girts Kaugars, both of Kalamazoo, Mich.

[73] Assignee: The Upjohn Company, Kalamazoo, Mich.

[22] Filed: May 20, 1974

[21] Appl. No.: 471,235

[52] U.S. Cl. ................................................ 424/327
[51] Int. Cl.² ........................ A01N 9/20; A01N 9/24
[58] Field of Search .................................... 424/327

[56] References Cited
OTHER PUBLICATIONS
Chemical Abstracts, Vol. 72 (1970), p. 78682e.

*Primary Examiner*—V. D. Turner
*Attorney, Agent, or Firm*—John J. Killinger; Roman Saliwanchik

[57] ABSTRACT

This invention relates to a new method of using and formulations of pyruvoyl chloride phenylhydrazones of the formula

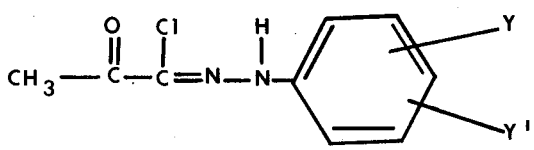

wherein Y is selected from the group consisting of chloro, bromo, nitro and trifluoromethyl and Y' has the same meaning as Y and in addition hydrogen, that have been found to be effective broad spectrum anthelmintics for suppressing parasitic worms in animals. The compounds are readily prepared by conventional chemical reactions.

7 Claims, No Drawings

METHOD OF TREATING ANIMALS AND FORMULATIONS THEREFOR

BRIEF SUMMARY OF THE INVENTION

This invention relates to a new method for killing and controlling (by suppressing growth and reproduction of) worms (Helminths), and new formulations for controlling worms in animals. The invention more particularly pertains to a new method for killing and controlling parasitic worms in animals and new anthelmintic formulations therefor, using pyruvoyl chloride phenylhydrazones of the formula

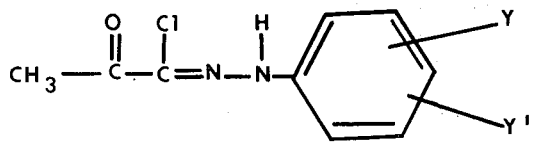

wherein Y is selected from the group consisting of chloro, bromo, nitro and trifluoromethyl and Y' has the same meaning as Y and in addition hydrogen.

One object of this invention is to describe how the aforesaid compounds (I), above, can be used to curb helminth parasitism in animals. Another is to show various anthelmintic formulations of these pyruvoyl chloride phenylhydrazones (I), and how they can be administered to animals infected with worms, for killing and control of of the helminth parasites. The formulations of the invention can be administered to animals for therapeutic or prophylactic treatment of infections.

DETAILED DESCRIPTION

The following examples and preparations are illustrative of the manner of making and using the invention and set forth the best mode contemplated by the inventors of carrying it out, but are not to be construed as limiting the scope thereof, as obvious modifications and equivalents will be apparent to those skilled in the art, and the invention is therefore to be limited only by the scope of the appended claims.

The pyruvoyl chloride phenylhydrazones (I) employed in the method and formulations of this invention, for example, pyruvoyl chloride 1-[(2,4-dichlorophenyl)hydrazone], pyruvoyl chloride 1-[(p-chlorophenyl)hydroazone], pyruvoyl chloride 1-[(o-chlorophenyl)hydrazone], pyruvoyl chloride 1-[(p-bromophenyl)hydrazone], pyruvoyl chloride 1-[(α,α,α-trifluoro-m-tolyl)hydrazone] and pyruvoyl chloride 1-[(2-chloro-4-nitrophenyl)hydrazone], are particularly effective against worms, particularly parasitic worms of animals, and more particularly parasitic helminths in ovines (sheep) and canines (dog). Observations in lambs naturally infected with Haemonchus, Cooperia, Moniezia, Nematodirus, Oesophagostomum, Oesteragia, Strongyloides, and/or Trichostronglus showed that the aforesaid compounds (I) are active at practical low dosages, and possess broad spectrum activity against both roundworms and tapeworms. Furthermore, the aforesaid compounds and the remaining closely related compounds embraced by generic formual I, above, are also contemplated as useful for killing and controlling parasitic worms in bovines, equines, porcines, aves, canines, felines, piscenes and other animals.

A preliminary test was carried out by maintaining worm infected lambs under satisfactory environmental conditions with feed and water available ad libitum. Pretreatment fecal examinations were made in order to characterize and evaluate the parasitism of each animal. The presence of helminth ova was recorded in terms of the number of eggs per gram of feces. On the day of treatment, each lamb was weighed and a dosage for it calculated in terms of milligrams of compound (I) per kilogram of body weight. The calculated dosage of compound was pulverized and packed in a gelatin capsule and administered orally. Post-treatment fecal examinations were made, usually on the second, fifth, seventh and tenth days following the administration of each compound (I), and the presence of helminth ova in terms of the number of eggs per gram of feces recorded. The efficacy of representative pyruvoyl chloride phenylhydrazones (I) against various genera of helminths in sheep and dogs is shown in Examples 1 and 2, below.

| Example 1 | Pyruvoyl chloride 1-[(2,4-dichlorophenyl)hydrazone] (I) Sheep; weight 32.7 kg. dosage 250 mg./kg. (8.18 g.) | | |
|---|---|---|---|
| Sample Number | Haem-onchus | Nemato-dirus | Tape worm |
| 1 | 12,300 | 500 | — |
| 2 | 10,900 | 300 | — |
| 3 | 4,400 | 400 | 200 |
| Compound administered | | | |
| 1 | 4,400 | — | — |
| 2 | — | — | 200 |
| 3 | — | — | — |
| 4 | — | — | — |

| Example 2 | Pyruvoyl chloride 1-[(2-chloro-4-nitrophenyl)hydrazone] (I) Dog; weight 5.0 kg; dosage 30 mg./kg. |
|---|---|
| Sample Number | Ancyl-ostoma |
| 1 | 2,100 |
| 2 | 3,200 |
| Compound administered | |
| 1 | 600 |
| 2 | 700 |

From an evaluation of the foregoing test results, it is apparent that the pyruvoyl chloride hydrazones (I) of this invention set forth in the foregoing examples are established as useful for killing and controlling worms in sheep and dogs. Furthermore, the aforesaid specific compounds and the remaining closely related compounds embraced by generic formula I, above, are efficacious anthelmintic agents.

In the foregoing tests, the pyruvoyl chloride phenylhydrazones (I) were administered orally as a finely divided solid (a powder) in a gelatin capsule. This uncomplicated form and route of administration is convenient for the compounds of this invention because they are solids at room temperature and they are not very soluble in water. A single dose was administered, but multiple doses can be used.

Other forms and routes of administration, and other formulations of the active ingredient are contemplated as embodiments of this invention. For example, aqueous or oil suspensions can be administered orally, or the compounds can be formulated with a solid carrier for feeding. Furthermore, an oil suspension can be converted into an aqueous emulsion by mixing with water and injecting the emulsion intramuscularly, subcutaneously or into the peritoneal cavity.

Pure compounds, mixtures of the active compounds, or combinations thereof with a solid carrier can be administered in the animal's food, or administered in the form of tablets, pills, a paste, boluses, wafers, and other conventional unit dosage forms. All of these various forms of active compounds of this invention can be prepared using physiologically acceptable carriers and known methods of formulation and manufacture.

Representative solid carriers conveniently available and satisfactory for physiologically acceptable, unit dosage formulations include corn starch, powdered lactose, powdered sucrose, talc, stearic acid, magnesium stearate, finely divided bentonite, and the like. The active agent can be mixed with a carrier in varying proportions from, for example, about 0.001 per cent by weight in animal food to about 90 or 95 per cent or more in a tablet or capsule. In the latter form, one might use no more carrier than sufficient to bind the particles of active compound.

The compounds of this invention should be mixed with animal feeds, in a way that will avoid degradation of the compound. The chlorine atom on the carbonyl carbon is substantially reactive, and amino groups and enzymes present in a feed might promote degradation. Certain kinds of animal feeds such as whole oats will give no problem, but others such as ground feed mixes can. Accordingly, administration to animals via their feed will require some information, judgment, and evaluation.

In general, the compounds can be formulated in stable powders or granules for mixing in an amount of feed for a single feeding or enough feed for one day and thus obtain therapeutic efficacy without complication. It is the prepared and stored feeds or feed premixes that require care. A recommended practice is to coat a granular formulation to protect and preserve the active ingredient. A prepared hog-feed containing about 0.2% of the active compound will provide a dosage of about 100 mg. per kg. body weight for each 100 lb. pig in its daily ration.

A solid diluent carrier need not be a homogeneous entity, but mixtures of different diluent carriers can be used. Moreover, formulations with a solid carrier can include small proportions of adjuvants such as water; alcohols; protein solutions and suspensions like skimmed milk; edible oils; sugar solutions, e.g., syrups; and organic adjuvants such as propylene glycols, sorbitol, glycerol, diethyl carbonate, and the like.

The solid carrier formulations for the invention are conveniently prepared in unit dosage forms, to facilitate administration to animals. Accordingly, several large boluses (about 20 g. weight) amounting to about 54 g. of active compound would be required for a single dosage to a 900 lb. horse at a dosage rate of 50 mg./kg. of body weight. Similarly, a 60 lb. lamb at a dosage rate of 100 mg./kg. of body weight would require a pill, capsule, or bolus containing about 2.7 g. of active compound. A small dog, on the other hand, weighing about 20 lbs., would require a total dosage of about 225 mg. at a dosage rate of 25 mg./kg. of body weight. The solid, unit dosage forms can be conveniently prepared in various sizes and concentrations of active ingredient, to accommodate treatment of the various sizes of animals that are parasitized by worms.

Liquid formulations can also be used. Representative liquid formulations include aqueous (including isotonic saline) suspensions, oil solutions and suspensions, and oil in water emulsions. Aqueous suspensions are obtained by dispersing the active compound in water, preferably including a suitable surface-active dispersing agent such as a cationic, anionic, or non-ionic surface-active agents. Representative suitable ones are polyoxyalkylene derivatives of fatty alcohols and of sorbitan esters, and glycerol and sorbitan esters of fatty acids. Various dispersing or suspending agents can be included and representative ones are synthetic and natural gums, tragacanth, acacia, alginate, dextran, gelatin, sodium carboxymethylcellulose, methylcellulose, polyvinylpyrrolidone, and the like. The proportion of the active compound in the aqueous suspensions of the invention can vary from about 1% to about 20% or more.

Oil solutions are prepared by mixing the active compound and an oil, e.g., an edible oil such as cotton seed oil, peanut oil, coconut oil, modified soybean oil, and sesame oil. Usually, solubility in oil will be limited and oil suspensions can be prepared by mixing additional finely divided compound in the oil.

Oil in water emulsions are prepared by mixing and dispersing an oil solution or suspension of the active compound in water preferably aided by surface-active agents and dispersing or suspending agents as indicated above.

In general, the formulations of this invention are administered to animals so as to achieve therapeutic or prophylactic levels of the active compound. At present, it is known that 100 mg./kg. of body weight in lambs will effectively combat a wide variety of parasitic worms. Much lower effective dosages are contemplated, e.g., in the range of 25 to 75 mg./kg. of body weight.

In other animals, and for other kinds of parasitic worms, definitive dosages can be proposed. Contemplated are dosage rates of about 1 mg. to about 800 mg. per kg. of body weight. A preferred, contemplated range of dosage rates is from about 5 mg. to about 400 mg. per kg. of body weight. In this regard, it should be noted that the concentration of active compound in the formulation selected for administration is in many situations not critical. One can administer a larger quantity of a formulation having a relatively low concentration and achieve the same therapeutic or prophylactic dosage as a relatively small quantity of a relatively more concentrated formulation. More frequent small dosages will likewise give results comparable to one large dose. Unit dosage forms in accordance with this invention can have anywhere from less than 10 mg. to 300 g. of active compound per unit.

If desired the solid unit dosage forms of this invention including pellets and granules can be coated so as to provide timed release in the digestive system of animals. Such laminated or enteric coated forms are prepared by appropriately applying to a pill or bolus a polymeric acid or a mixture of a polymeric acid with shellac, and cetyl alcohol, cellulose acetate, or styrene maleic acid copolymer.

The pyruvoyl chloride phenylhydrazones (I) employed in Examples 1 and 2 and other compounds embraced by generic formula I, above, can be prepared by chemical syntheses known in the art, e.g., by direct chlorination with limited or excess amounts of chlorine. This method cannot be used when the phenyl moiety of the desired compound is unsubstituted. Pyruvoyl chloride phenylhydrazones (I) can also be prepared by reacting a benzene diazonium chloride with chloroacetone, said diazonium compounds being prepared from a substituted aniline by diazotization, e.g., with sodium nitrite in the cold. Another convenient and efficient method broadly applicable for preparing the compounds (I) of this invention, is to react 3-chloropentane-2,4-dione with a benzene diazonium chloride in aqueous solution. A preferred method for preparing the compounds (I) of this invention is by chlorination of a pentanetrione phenylhydrazone, in accordance with the procedure set forth immediately below.

A 2,3,4-pentanedione-3-phenylhydrazone (III) is reacted with a hypochlorite, e.g., tert. butyl hypochlorite to produce a 3-chloro-3-phenylazo-2,4-diketone (II) intermediate, which on solvolysis with an alcohol, e.g., methanol or ethanol, gives a desired pyruvoyl chloride phenylhydrazone (I) employed in this invention, as is illustratively represented by the following sequence of formulae:

The hydrolysis step of this process is effected with a mild hydrolytic reagent such as methanol or ethanol, dilute aqueous sodium hydroxide, or morpholine. The intermediate 3-chloro-3-phenylazo-2,4-pentanedione (II) is advantageously separated from the reaction medium by conventional procedures such as removing the organic solvent by evaporation. The residue is then dissolved in methanol or ethanol for hydrolysis. The desired pyruvoyl chloride phenylhydrazone (I) separates from the alcoholic medium and can readily be recovered by conventional techniques such as filtration and solvent evaporation.

The 2,3,4-pentanetrione-3-phenylhydrazone (III) starting compounds of this process are readily prepared by reacting 2,4-pentanedione with a benzene diazonium chloride in accordance with methods known in the art, e.g., Chem. Ber. 21, 1702 and 35, 2188.

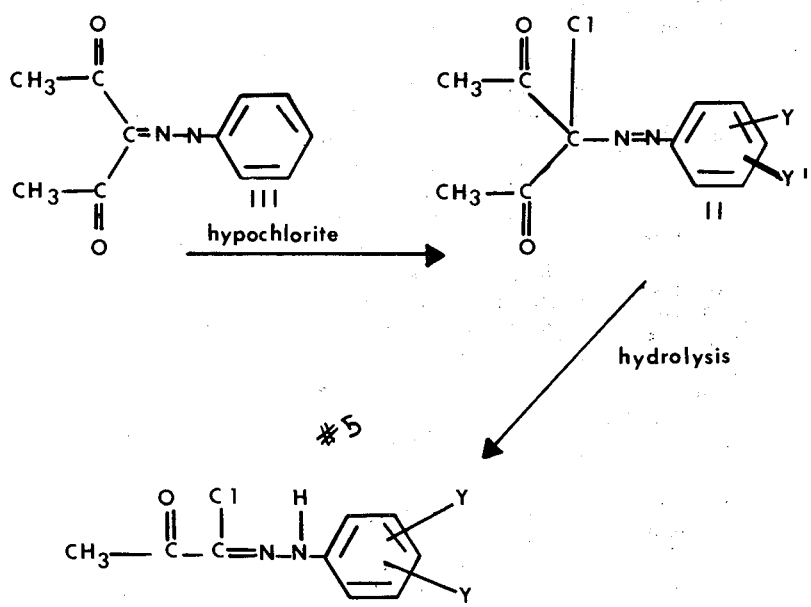

wherein Y and Y' have the same meaning as above.

The first step of this process is effected by adding one equivalent (or an excess, if desired) of the chosen alkyl (or alkaline earth metal) hypochlorite to an organic solution of an appropriate 2,3,4-pentanetrione-3-phenylhydrazone (III). Chloroform is a preferred solvent, although ethanol, benzene, toluene or carbon tetrachloride can be used. The alkyl hypochlorites are liquids and soluble in the aforesaid solvents. The reaction is often exothermic, especially when the phenyl ring is unsubstituted; for example, 2,3,4,-pentanetrione 3-phenylhydrazone is chlorinated within minutes using tert.-butyl hypochlorite. On the other hand, 2,3,4-pentanetrione 3-[(2,4-dichlorophenyl)hydrazone] (III) requires several hours for chlorination. Accordingly, the reaction mixture can be warmed gently in order to speed the reaction when there are deactivative substituents on the phenyl ring. The hypochlorite reagent is aggressive enough to require caution in its use in this reaction. The alkaline earth metal hypochlorites are solids and are dissolved in water for addition to the organic solution of the pentanetrione phenylhydrazone (III). The reaction proceeds in the two-phase system with the chlorinated phenylazo compound (II) remaining in the organic phase.

EXAMPLE 3

Pyruvoyl chloride 1-[(2,4-dichlorophenyl)hydrazone] (I)

Part A 2,3,4-Pentanetrione 3-[(2,4-dichlorophenyl)hydrazone] (III)

To a chilled (0° C.) suspension of 2,4-dichloroaniline (480 g., 3 moles) in 675 ml. concentrated hydrochloric acid diluted with 500 ml. water and containing crushed ice there is added a solution consisting of 210 g. sodium nitrite and 700 ml. of water. This reaction mixture is stirred for 10 minutes before filtering. There is thus obtained a clear yellow solution of the benzenediazonium chloride. To this solution there is added a solution consisting of 450 g. sodium acetate and 700 ml. water. Then a solution consisting of 300 g. 2,4-pentanedione, 120 g. sodium hydroxide, and 1500 ml. 50% aqueous ethanol is added. The yellow precipitate that forms is collected on a filter, washed thoroughly with water, and dried. There is thus obtained 690 g. (85% yield) of 2,3,4-pentanetrione 3-[(2,4-dichlorophenyl)-hydrazone] (III).

Part B

Pyruvoyl chloride 1-[-(2,4-dichlorophenyl)hydrazone] (I)

A 420 g. quantity (1.5 mole) of 2,3,4-pentanetrione 3-[(2,4-dichlorophenyl)hydrazone] (III) (prepared in Part A, above) is suspended in 2.5 l. chloroform and 230 ml. (1.92 mole) tert-butyl hypochlorite is added. This reaction mixture is stirred for 18 hours during which time a clear solution is formed. The chloroform is removed by evaporation under reduced pressure, and a gummy residue of the 3-chloro-3-phenylazo-2,4-diketone intermediate (II) obtained. The gummy residue is dissolved in 2 l. methanol and the solution heated to 60° C. An exothermic reaction develops and crystals begin to separate. After cooling to 20° C. the crystals are collected on a filter, washed with methanol, and dried. There is thus obtained 357 g. (88% yield) of pyruvoyl chloride 1-[(2,4-dichlorophenyl)hydrazone] (I) having a melting point at 117° to 119° C.

EXAMPLE 4

Pyruvoyl chloride 1-[(p-chlorophenyl)hydrazone] (I)

Part A

Pyruvoyl chloride phenylhydrazone

To 102.4 g. of 2,3,4-pentanetrione 3-(phenylhydrazone) dissolved in 250 ml. of chloroform and cooled to about 15° C., 100 ml. of tert. butyl hypochlorite is added. The temperature rises to 25° C. and is allowed to cool to 15° C. before the next addition of 60 ml. (0.5 mole). No starting material remains and the solvent of the reaction mixture is evaporated to give a gum, which is dissolved in 250 ml. of methanol and then heated to about 40° C. The temperature of the solution varies from about 40° to about 60° C. for about 15 minutes, and is then cooled to about 0° C., and the precipitate filtered off and washed with cold methanol. The weight of the precipitate that melts at 134° to 136° C. is 71.3 g. (73% yield). A 10 g. portion of this compound is recrystallized from equal parts of ethyl acetate and Skellysolve B (hexanes) to give pure pyruvoyl chloride 1-(phenylhydrazone) melting at 135 to 137° C.

Anal. Calcd. for $C_9H_9ClN_2O$: C, 54.97; H, 4.61; Cl, 18.03; N, 14.25. Found: C, 55.41; H, 4.77; Cl, 17.38; N, 14.20.

Part B

Pyruvoyl chloride 1-[(p-chlorophenyl)hydrazone] (I)

To 19.6 g. of pyruvoyl chloride 1-(phenylhydrazone) dissolved in 500 ml. of chloroform, 12.4 cc. of tert. butyl hypochlorite is added at 6° C. with the reaction mixture kept in an ice bath. After about 3 hours the reaction mixture is cooled to about −10° C. and 8.85 g. of crystals (melting at 169° to 173° C.) filtered off. Concentration of the mother liquors to a volume of 40 ml. followed by cooling at 0° C. for about 17 hours gives a further 5.5 g. of crystals. The two crops of crystals weighing 13.85 g. are pooled and recrystallized from 150 ml. of ethyl acetate. This material is dissolved in 200 ml. of ethyl acetate and allowed to cool slowly to give 8.4 g. of large rods of crystalline pyruvoyl chloride 1-[(p-chlorophenyl)hydrazone] (I) melting at 172° to 174° C.

Anal. Calcd. for $C_9H_8Cl_2N_2O$: C, 46.77; H, 3.49; N, 12.13; Cl, 30.69. Found: C, 47.07; H, 3.24; N, 12.22; Cl, 31.05.

Pyruvoyl chloride 1-[(p-chlorophenyl)hydrazone] (I) can also be prepared by the procedure that follows.

A solution kept at −60° C. and consisting of 8.2 g. (0.05 mole) of pyruvaldehyde phenylhydrazone and 100 ml. of chloroform is stirred continuously while 4.5 ml. of chlorine is added. The reaction mixture is allowed to warm to 15° C. over a period of about 1 hour, and the chloroform then removed by evaporation. The thus obtained solid residue is washed with methanol and recrystallized from ethyl acetate to give 5.4 g. of pyruvoyl chloride 1-[(p-chlorophenyl)hydrazone] (I), having a melting point of 168° to 172° C.

EXAMPLE 5

Pyruvoyl chloride 1-[(o-chlorophenyl)hydrazone] (I)

Part A

2,3,4-Pentanetrione 3-[(o-chlorophenyl)hydrazone] (III)

To a chilled (0° C.) suspension of 51 ml. of o-chloroaniline in 110 ml. of concentrated hydrochloric acid diluted with 839 ml. of water containing crushed ice, 36 g. of sodium nitrite is added. This reaction mixture is stirred and filtered to give a clear solution of the benzenediazonium chloride. To this solution there is added (while stirring) 100 g. of sodium acetate, then a solution of 50 ml. of 2,4-pentanedione in 500 ml. of water containing 20 g. of sodium hydroxide. The precipitate that forms is separated by filtration and an aliquot recrystallized from methanol and cooled to 0° C. to give 11.1 g. of 2,3,4,-pentanetrione 3-[(o-chlorophenyl)hydrazone] (III).

Part B

Pyruvoyl chloride 1-[(o-chlorophenyl)hydrazone] (I)

The 2,3,4-pentanetrione 3-[(o-chlorophenyl)hydrazone] (III) (prepared in Part A, above) is dissolved in 50 ml. of chloroform and 6 ml. of tert. butyl hypochlorite added at 0° C. This reaction mixture is allowed to stand at room temperature for about 1 hour and the chloroform evaporated to give a residue of the 3-chloro-3-phenylazo-2,4-diketone intermediate (II). The residue is dissolved in 50 ml. of methanol and the solution heated to about 50° C. An exothermic reaction (about 70° C.) develops and solid material separates. The solid is filtered off to give 7.7 g. of product (I) having a melting point of 132 to 135° C. A second crop of this compound (I) weighing 1 g. and melting at 129 to 133° C. is separated from the mother liquors. Recrystallization of the 7.7 g. portion from 50 ml. of ethyl acetate gives pure pyruvoyl chloride 1-[(o-chlorophenyl)hydrazone] (I), which after cooling to 0° C. weighs 4.6 g. and has a melting point of 133 to 135° C.

Anal. Calcd. for $C_9H_8Cl_2N_2O$: C, 46.77; H, 3.49; Cl, 30.69; N, 12.13. Found: C, 46.71; H, 3.83; Cl, 30.37, N, 12.21.

EXAMPLE 6

Pyruvoyl chloride 1-[(p-bromophenyl)hydrazone] (I)

Part A

2,3,4-Pentanetrione 3-[(p-bromophenyl)hydrazone] (III)

To 86 g. (0.5 mole) of p-bromoaniline sufficient glacial acetic acid is added to dissolved it. The solution (kept at 0° C.) has 225 ml. of concentrated hydrochloric acid added to it, then 36 g. (0.52 mole) of sodium nitrite in 100 ml. of water is added, followed by 200 g. of sodium acetate. To this solution, 50 g. (0.5 mole) of 2,4-pentanedione in a solution of 20 g. of sodium hydroxide in 200 ml. of water is added. After about 1 hour the solid that precipitates is collected, washed with water, dried and recrystallized from ethanol: benzene to give 75 g. of 2,3,4-pentanetrione 3-[(p-bromophenyl)hydrazone] (III), melting at 141° to 142° C. An analytical sample recrystallized from absolute ethyl acetate gives 5.7 g. of product (III) melting at 141° to 142° C.

Anal. Calcd. for $C_{11}H_{11}BrN_2O_2$: C, 46.66; H, 3.92; Br, 28.23; N, 9.90. Found: C, 46.62; H, 4.18; N, 9.95.

Part B.

Pyruvoyl chloride 1-[(p-bromophenyl)hydrazone] (I)

To 42.5 g. (0.15 mole) of 2,3,4-pentanetrione 3-[(p-bromophenyl)hydrazone] (III) (prepared in Part A, above) 70 ml. of chloroform and 30 ml. (0.25 mole) of tert. butyl hypochlorite are added, and the reaction mixture allowed to stand at room temperature for about 5 hours. The chloroform is removed to give a residue of the 3-chloro-3-phenylazo-2,4-diketone intermediate (II). The residue is dissolved in 80 ml. of methanol and the solution heated until reaction begins. Solid material weighing 38.5 g. comes out of solution and is recrystallized from chloroform to give 16.2 g. of pyruvoyl chloride 1-[(p-bromophenyl)hydrazone] (I) having a melting point of 170° to 171° C.

Anal. Calcd. for $C_9H_8BrClN_2O$: C, 39.23; H, 2.93; N, 10.17. Found: C, 39.24; H, 3.05; N, 10.25.

EXAMPLE 7

Pyruvoyl chloride 1-[(α,α,α-trifluoro-m-tolyl)hydrazone] (I); also named pyruvoyl chloride 1-[(m-trifluoromethyl)hydrazone]

Part A 2,3,4-Pentanetrione 3-[(α,α,α-trifluoro-m-tolyl)hydrazone] (III)

To a cold (0° C.) solution of 80 ml. of concentrated hydrochloric acid and 300 ml. of water, there is added a solution of 49.2 g. (0.305 mole) of m-trifluoromethylaniline and then a solution of 22.1 g. (0.32 mole) of sodium nitrite in 100 ml. of water. The resulting benzenediazonium chloride solution is filtered to remove a small amount of insoluble material. To this solution is added 100 g. of sodium acetate followed by a solution of 30.5 g. (0.305 mole) of 2,4-pentanedione and 12.2 g. (0.305 mole) of sodium hydroxide in 150 ml. of water. After about 0.5 hour the solids that form are filtered, washed with water, partly dried on the filter funnel and recrystallized from 450 ml. of ethanol to yield 76.6 g. (92% yield) of product (III), melting at 107.5° to 109° C. An analytical sample is obtained by recrystallization from ethanol to give pure 2,3,4-pentanetrione 3 -[(α,α,α-trifluoro-m-tolyl)hydrazone] (III), melting at 108 to 109.5°C. with slight softening at 102° C.

Anal. Calcd. for $C_{12}H_{11}F_3N_2O_2$: C, 52.94; H, 4.07; F, 20.94; N, 10.29; Found: C, 52.77; H, 4.03; F, 21.86; N, 10.45.

Part B

Pyruvoyl chloride 1-[α,α,α-trifluoro-m-tolyl)hydrazone] (I)

To 54.4 g. (0.2 mole) of 2,3,4-pentanetrione 3-[(α,α,α-trifluoro-m-tolyl)hydrazone] (III) (prepared in Part A, above) dissolved in 250 ml. of chloroform, 25 ml. (0.208 mole) of tert. butyl hypochlorite is added at from about 15° to about 19° C. After about 2.5 hours, TLC (thin layer chromatography) with benzene shows the reaction to have gone to completion. The solvent is removed under reduced pressure and the residue of the thus produced 3-chloro-3-phenylazo-2,4-diketone intermediate (II) dissolved in about 150 ml. of methanol. This solution is heated to about 60° C., whereupon a vigorous reaction occurs. When this subsides, the suspension is diluted with methanol, heated to boiling, filtered and allowed to crystallize from a total volume of about 350 ml. to yield 40.9 g. (77.4% yield) of pyruvoyl chloride 1-[(α,α,α-trifluoro-m-tolyl)hydrazone] (I) melting at 166 to 167.5° C. A second crop off product (I) gives 7.4 g. (14% yield) having a melting point of 165° to 167° C. An analytical sample recrystallized from ethanol has a melting point of 166 to 167.5° C.

Anal. Calcd. for $C_{10}H_8ClF_3N_2O$: C, 45.38; H, 3.05; N, 10.59; Found: C, 45.54; H, 2.89; N, 10.96.

EXAMPLE 8

Pyruvoyl chloride 1-[(2-chloro-4-nitrophenyl)hydrazone] (I)

To a cold (0° C.) suspension of 41 g. (0.3 mole) of 2-chloro-4-nitroaniline in 100 ml. of concentrated hydrochloric acid diluted with 200 ml. of water, a solution of 21 g. (0.3 mole) of sodium nitrite in 100 ml. of water is added. The resulting benzenediazonium chloride solution is filtered. The filtered solution is stirred, 272 g. of sodium acetate trihydrate added and then 40.2 g. (0.3 mole) of 3-chloropentane-2,4-dione added. After about 30 minutes the solution is extracted with chloroform, the chloroform layer washed with water, evaporated and refluxed briefly with methanol to decompose the azo intermediate compound of the formula

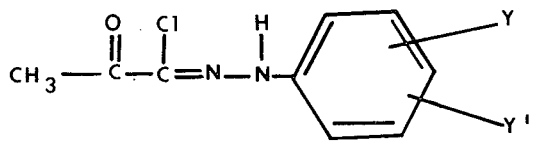

On cooling the methanol solution, a precipitate of pyruvoyl chloride 1-[(2-chloro-4-nitrophenyl)hydrazone] (I) having a melting point of 140° to 143° C. is obtained.

Following the procedures of Examples 3 and 5 through 8 but substituting other anilines, such as 1. 2-bromo-4-chloroaniline,
2. 2,6-dichloroaniline,
3. 3,5-dichloroaniline,
4. 2,4-dibromoaniline,
5. 2-bromo-4-nitroaniline,
6. 5-bromo-2-nitroaniline,
7. 2-bromoaniline,
8. m-chloroaniline,
9. p-trifluoromethylaniline,
10. 2-nitroaniline,
11. 2-bromo-4-trifluoromethylaniline
12. 5-chloro-2-trifluoromethylaniline,
13. 2,4-dinitroaniline 14. 2,4-bis (trifluoromethyl)aniline
15. 2-fluoromethyl-4-nitroaniline, and the like, yields, respectively, 1. Pyruvoyl Chloride 1-[(2-bromo-4-chlorophenyl)hydrazone] (I),
2. pyruvoyl chloride 1-[(2,6-dichlorophenyl)hydrazone] (I),
3. pyruvoyl chloride 1-[(3,5-dichlorophenyl)hydrazone] (I),
4. pyruvoyl chloride 1-[(2,4-dibromophenyl)hydrazone] (I),
5. pyruvoyl chloride 1-[(2-bromo-4-nitrophenyl)hydrazone] (I),
6. pyruvoyl chloride 1-[(5-bromo-2-nitrophenyl)hydrazone] (I),
7. pyruvoyl chloride 1-[(2-bromophenyl)hydrazone] (I),
8. pyruvoyl chloride 1-[(m-chlorophenyl)hydrazone] (I),
9. pyruvoyl chloride 1-[(p-trifluoromethylphenyl)hydrazone] (I),
10. pyruvoyl chloride 1-[(2-nitrophenyl)hydrazone] (I),
11. pyruvoyl chloride 1-[2-bromo-4-trifluoromethylphenyl)hydrazone] (I),
12. pyruvoyl chloride 1-[(5-chloro-2-trifluoromethylphenyl)hydrazone] (I),
13. pyruvoyl chloride 1-[(2,4-dinitrophenyl)hydrazone] (I),
14. pyruvoyl chloride 1-[(2,4-bis(trifluoromethyl)phenyl)hydrazone] (I),
15. pyruvoyl chloride 1-[(2-fluoromethyl-4-nitrophenyl)hydrazone] (I), and the like

We claim:
1. A method of killing and controlling parasitic worms in animals which comprises administering to an animal a therapeutic or prophylactic dosage of a pyruvoyl chloride phenylhydrazone of the formula

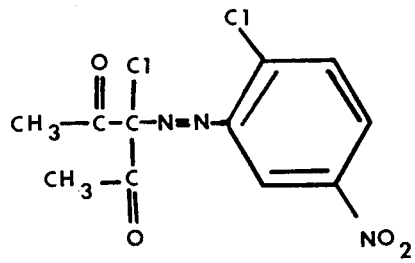

wherein Y is selected from the group consisting of chloro, bromo, nitro and trifluoromethyl and Y' has the same meaning as Y and in addition hydrogen.

2. A method in accordance with claim 1 wherein the compound administered is pyruvoyl chloride 1-[(2,4-dichlorophenyl)hydrazone].

3. A method in accordance with claim 1 wherein the compound administered is pyruvoyl chloride 1-[(p-chlorophenyl)hydrazone].

4. A method in accordance with claim 1 wherein the compound administered is pyruvoyl chloride 1-[(o-chlorophenyl)hydrazone].

5. A method in accordance with claim 1 wherein the compound administered is pyruvoyl chloride 1-[(p-bromophenyl)hydrazone].

6. A method in accordance with claim 1 wherein the compound administered is pyruvoyl chloride 1-[(m-trifluoromethylphenyl)hydrazone].

7. A method in accordance with claim 1 wherein the compound administered is pyruvoyl chloride 1-[(2-chloro-4-nitrophenyl)hydrazone].

* * * * *

UNITED STATES PATENT AND TRADEMARK OFFICE
CERTIFICATE OF CORRECTION

PATENT NO. : 3,932,662

DATED : January 13, 1976

INVENTOR(S) : Malcolm W. Moon, Girts Kaugars

It is certified that error appears in the above-identified patent and that said Letters Patent are hereby corrected as shown below:

ABSTRACT, Formula No. "I" should be inserted by formula; Column 1, line 22: Formula No. "I" should be inserted by formula; lines 57-59 "Haemonchus, Cooperia, Moniezia, Nematodirus, Oesophagostomum Oesteragia, Strongyloides, and/or Trichostronglus" should read --Haemonchus, Cooperia, Moniezia, Nematodirus, Oesophagostomum, Oesteragia, Strongyloides, and/or Trichostronglus--. Column 5, Formula

5

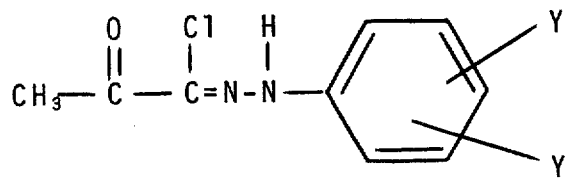

should read

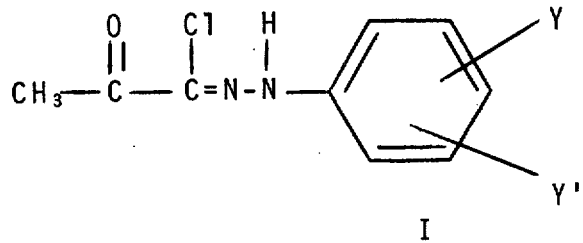

I

UNITED STATES PATENT AND TRADEMARK OFFICE
CERTIFICATE OF CORRECTION

PATENT NO. : 3,932,662
DATED : January 13, 1976
INVENTOR(S) : Malcolm W. Moon, Girts Kaugars It is certified that error appears in the above-identified patent and that said Letters Patent are hereby corrected as shown below:

Column 10, Formula

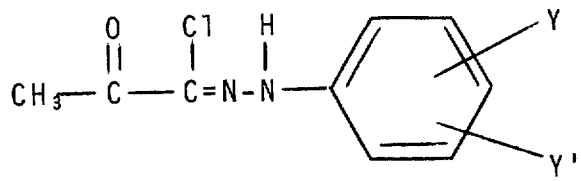

should read

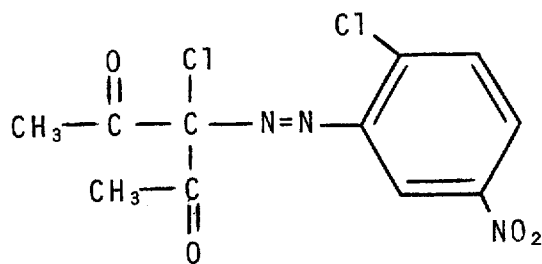

Column 11, line 24 "1-[2-" should read -- 1-[(2- --. Column 12, Formula

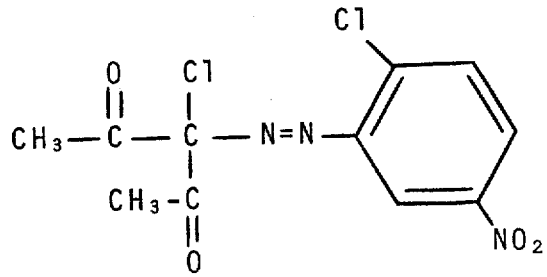

UNITED STATES PATENT OFFICE
CERTIFICATE OF CORRECTION

Patent No. 3,932,662  Dated January 13, 1976

Inventor(s) Malcolm W. Moon, Girts Kaugars  Page 3 of 3

It is certified that error appears in the above-identified patent and that said Letters Patent are hereby corrected as shown below:

should read

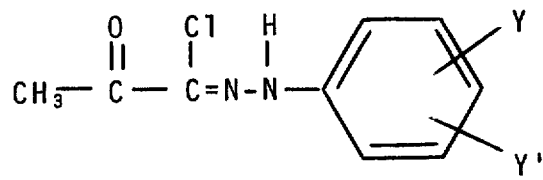

𝔖igned and 𝔖ealed this

Seventeenth Day of August 1976

[SEAL]

Attest:

RUTH C. MASON  
*Attesting Officer*

C. MARSHALL DANN  
*Commissioner of Patents and Trademarks*